(12) United States Patent
Streeper et al.

(10) Patent No.: US 12,329,735 B2
(45) Date of Patent: *Jun. 17, 2025

(54) AZELAIC ACID ESTERS IN THE TREATMENT OF INSULIN RESISTANCE

(71) Applicant: NEW FRONTIER LABS, LLC, San Antonio, TX (US)

(72) Inventors: Robert T. Streeper, San Antonio, TX (US); Elzbieta Izbicka, San Antonio, TX (US)

(73) Assignee: NEW FRONTIER LABS, LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/318,586

(22) Filed: May 12, 2021

(65) Prior Publication Data

US 2021/0260014 A1 Aug. 26, 2021

Related U.S. Application Data

(60) Division of application No. 16/267,338, filed on Feb. 4, 2019, now Pat. No. 11,026,912, which is a continuation of application No. 15/491,937, filed on Apr. 19, 2017, now Pat. No. 10,251,857.

(60) Provisional application No. 62/325,381, filed on Apr. 20, 2016.

(51) Int. Cl.
| | |
|---|---|
| *A61K 31/225* | (2006.01) |
| *A61K 9/00* | (2006.01) |
| *A61K 31/23* | (2006.01) |
| *A61K 31/337* | (2006.01) |
| *A61K 31/573* | (2006.01) |
| *A61K 45/06* | (2006.01) |

(52) U.S. Cl.
CPC .......... *A61K 31/225* (2013.01); *A61K 9/0019* (2013.01); *A61K 9/0053* (2013.01); *A61K 31/23* (2013.01); *A61K 31/337* (2013.01); *A61K 31/573* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,017,539 A | 4/1977 | Bosies et al. | |
| 5,594,015 A | 1/1997 | Kurtz et al. | |
| 6,627,223 B2 | 9/2003 | Percel et al. | |
| 7,363,076 B2 | 4/2008 | Yun et al. | |
| 7,625,557 B2 | 12/2009 | Edelson | |
| 7,713,929 B2 | 5/2010 | Steiner et al. | |
| 8,093,017 B2 | 1/2012 | Pugia | |
| 8,440,217 B1 * | 5/2013 | El-Naggar | B29D 11/00096 604/289 |
| 9,023,887 B2 * | 5/2015 | Singh | A61P 1/18 514/230.5 |
| 10,251,857 B2 | 4/2019 | Streeper et al. | |
| 2002/0004489 A1 * | 1/2002 | Shi | A61P 15/00 435/325 |
| 2007/0048371 A1 * | 3/2007 | Shojaei | A61P 25/00 424/464 |
| 2008/0051373 A1 * | 2/2008 | Lichtenberger | A61K 31/662 514/114 |
| 2009/0326069 A1 * | 12/2009 | Streeper | A61P 29/00 560/190 |
| 2011/0002900 A1 | 1/2011 | Mingrone et al. | |

FOREIGN PATENT DOCUMENTS

| | | |
|---|---|---|
| KR | 101593539 B1 | 10/2016 |
| WO | 2006/074379 A2 | 7/2006 |
| WO | 2010/005521 A1 | 1/2010 |
| WO | 2013/158541 A1 | 10/2013 |

OTHER PUBLICATIONS

Chaudhuri et al. J Clin Endocrinol Metab, Jan. 2012, 97(1):198-207. (Year: 2012).*
Passi et al. Acta Derm Venerol (Stockh) 1989; Suppl 143: 8-13. (Year: 1989).*
Muthulakshmi S. et al., "Gene expression profile of high-fat diet-fed C57BL/6J mice: in search of potential role of azelaic acid", Journal of Physiology and Biochemistry, Jan. 11, 2015, pp. 29-42, vol. 71(1).
Zareian P. et al., "Serum Interleukin 17 in Type 2 Diabetes Mellitus", Journal of Archives in Military Medicine, Sep. 1, 2014, pp. 1-4, Article No. e24689, vol. 2(4).
Paglialunga et al., "Adding to the spectrum of insulin sensitive populations for mixed meal tolerance test glucose eliability assessment", Journal of Diabetes & Metabolic Disorders, 2016, pp. 1-4, 15:57.
Traversy et al., "Alcohol Consumption and Obesity: An Update", Curr Obes Rep, 2015, pp. 122-130, vol. 4.
Patarrao et al., "Assessment of methods and indexes of insulin sensitivity", Rev Port Endocrinol Diabetes Melab., 2014, pp. 65-73, vol. 9(1 ).
Legio et al., "Blood Glucose Level, Alcohol Heavy Drinking and Alcohol Craving during Treatment for Alcohol Dependence: Results from the Combined Pharmacotherapies and Behavioral Interventions for Alcohol Dependence COMBINE) Study", Alcohol Clin Exp Res., Sep. 2009, pp. 1539-1544, 33(9).
Boden et al., "Excessive caloric intake acutely causes oxidative stress, GLUT 4 carbonylalion, and insulin resistance In healthy men", Sci Transl Med., Sep. 9, 2015, pp. 1-19, vol. 7(304).
Carr et al., "Temporal effects of ethanol consumption on energy homeostasis, hepatic steatosis and insulin sensitivity in mice", Alcohol Clin Exp Res., Jul. 2013, pp. 1091-1099, vol. 37(7).

(Continued)

*Primary Examiner* — Katherine Peebles
(74) *Attorney, Agent, or Firm* — Pillsbury Winthrop Shaw Pittman LLP

(57) ABSTRACT

A method of treating insulin resistance includes administering to a subject a pharmaceutical composition comprising diethyl azelate. For example, a method of treating insulin resistance includes orally administering to a subject a pharmaceutical composition that includes diethyl azelate at a dosage range from about 0.1 mg/kg/day to about 10 mg/kg/day.

17 Claims, 7 Drawing Sheets

(56) References Cited

OTHER PUBLICATIONS

Ramirez et al., "Chronic alcohol-induced hepatic insulin resistance and ER stress ameliorated by PPAR-o agonist treatment", J Gastroenterol Hepatol, Jan. 2013, pp. 179-187, vol. 28(1).

Kim et al., "Chronic Ethanol Consumption Inhibits Glucokinase Transcriptional Activity by Atf3 and Triggers Metabolic Syndrome in Vivo", The Journal of Biological Chemistry, Sep. 26, 2014, pp. 27065-07079, vol. 289 (39).

Kim et al., "Chronic Ethanol Consumption-induced Pancreatic Beta-Cell Dysfunction and Apoptosis through 3 Glucokinase Nitration and Its Down-regulation", The Journal of Biological Chemistry, Nov. 26, 2010, pp. 37251-37262, vol. 285(48).

Xiao et al., "Cytokines and Diabetes Research", Journal of Diabetes Research, Jan. 16, 2014, pp. 1-2, vol. 2014, Article ID 920613, Hindawi Publishing Corporation.

Lustig, Robert H., "Fructose: It's Alcohol Without the Buzz", American Society for Nutrition. Adv. Nutr., 2013, pp. 226-235, vol. 4.

Hirakawa et al., "Relationship between Alcohol Intake and Risk Factors for Metabolic Syndrome in Men", Intern Med., 2015, pp. 2139-2145, vol. 54.

Carrigan et al., "Hominids adapted to metabolize ethanol long before human-directed fermentation", PNAS, Jan. 13, 2015, pp. 458-463, vol. 112(2).

Iaconelli et al., "Effect of Oral Sebacic Acid on Postprandial Glycemia, Insulinemia, and Glucose Rate of Appearance in Type 2 Diabetes", Diabetes Care, Nov. 2010, pp. 2327-2332, vol. 33(11).

Steiner et al., "Impact of Alcohol on Glycemic Control and Insulin Action, Biomolecules", 2015, pp. 2223-2246, vol. 5.

Hatting et al., "Insulin regulation of gluconeogenesis", Ann. N.Y. Acad. Sci., 2018, pp. 21-35, vol. 1411.

Carr et al., "Insulin resistance in clinical and experimental alcoholic liver disease," Ann. N.Y. Acad. Sci., Sep. 2015, pp. 1-29, vol. 1353(1).

Kang, et al., "Chronic Ethanol-Induced Insulin Resistance is Associated With Macrophage Infiltration Into Adipose Tissue and Altered Expression of Adipocytokines", Alcohol Clin Exp Res, Sep. 2007, pp. 1581-1588, vol. 31(9).

Kim et al., "Alcoholism and Diabetes Mellitus", Diabetes & Metabolism Journal, 2012, pp. 108-115, vol. 36.

Kim et al., "Is an Oral Glucose Tolerance Test Still Valid for Diagnosing Diabetes Mellitus?", Diabetes & Metabolism Journal, 2016, pp. 118-128, vol. 40.

Besser et al., "Lessons From the Mixed-Meal Tolerance Test", Diabetes Care, Feb. 2013, pp. 195-201, vol. 36.

Lindtner et al., "Binge Drinking Induces Whole-Body Insulin Resistance by Impairing Hypothalamic Insulin Action", Sci Transl Med., Jan. 30, 2013, pp. 1-26, vol. 5(170).

U.S. Department of Health and Human Services Food and Drug Administration Center for Food Safety and Applied Nutrition, "Frequently Asked Questions About Medical Foods", May 2016, pp. 1-12, Second Edition.

Brodovicz et al., "Postprandial metabolic responses to mixed versus liquid meal tests in healthy men and men with type 2 diabetes", Diabetes Research and Clinical Practice, 2011, pp. 449-455, vol. 94.

Shelmet et al., "Ethanol Causes Acute Inhibition of Carbohydrate, Fat, and Protein Oxidation and Insulin Resistance", J. Clin. Invest., Apr. 1988, pp. 1137-1145, vol. 81.

Wan et al., "Ethanol Feeding Impairs Insulin-Stimulated Glucose Uptake in Isolated Rat Skeletal Muscle: Role of Gs alpha and cAMP", Alcoholism: Clinical and Experimental Research, Aug. 2005, pp. 1450-1456, vol. 29 (8).

Muthulakshmi et al., "Efficacy of azelaic acid on hepatic key enzymes of carbohydrate metabolism in high fat diet induced type 2 diabetic mice", Biochimie., 2013, pp. 1239-1244., vol. 95.

Fan et al., "Patterns of Alcohol Consumption and the Metabolic Syndrome", J. Clin. Endocrinol Metab, Oct. 2008, pp. 3833-3838, vol. 93(10).

Tura et al., "Shape of glucose, insulin, C-peptide curves during a 3-h oral glucose tolerance test: any relationship with the degree of glucose tolerance?", Am J Physiol Regul Integr Comp Physiol, Jan. 11, 2011, pp. R941-R948, vol. 300.

Conn et al., "Insulin sensitivity following exercise interventions: systematic review and meta-analysis of outcomes among healthy adults", J Prim Care Community Health, Jul. 2014, pp. 211-222, vol. 5(3).

Gao et al., "Fish oil supplementation and insulin sensitivity: a systematic review and meta-analysis", Lipids in Health and Disease, 2017, pp. 1-9, vol. 16(131).

Jamka et al., "The effect of vitamin D supplementation on insulin and glucose metabolism in overweight and obese individuals: systematic review with meta-analysis", Nature Scientific Reports, Nov. 6, 2015, pp. 1-20, vol. 5(16142).

Muniyappa et al., "Current approaches for assessing insulin sensitivity and resistance in vivo: advantages limitations, and appropriate usage", Am J Physiol Endocrinol Metab., Oct. 23, 2007, pp. E15-E26, vol. 294.

Tiwari, Priya, "presentation on Posology", accessed on Feb. 2, 2024, https://www.ramauniversity.ac.in/online-study-material/pharmacy/dpharma/2year/pharmaceutics-ii/lecture-4.pdf, Rama University, Kanpur, pp. 1-27.

* cited by examiner

** Dotted lines represent the 1 hour (180 mg/dL) and 2 hour (140 mg/dl) OGTT thresholds

AZELAIC ACID ESTERS IN THE TREATMENT OF INSULIN RESISTANCE

RELATED APPLICATIONS

This patent application is a division of, and claims the benefit of U.S. patent application Ser. No. 16/267,338, filed Feb. 4, 2019, which is a continuation of, and claims the benefit of U.S. patent application Ser. No. 15/491,937, filed Apr. 19, 2017, now U.S. Pat. No. 10,251,857, issued Apr. 9, 2019, which claims priority to U.S. Provisional Patent Application No. 62/325,381, filed Apr. 20, 2016. The entire content of the foregoing applications are incorporated herein by reference in their entirety, including all text, tables and drawings.

BACKGROUND

The present disclosure relates to methods for treating insulin resistance. In particular, the present disclosure relates to methods for treating, preventing, and/or reducing insulin resistance in a subject.

Insulin resistance is typically defined as failure of the cells of the body to respond to insulin. Inefficient insulin function affects skeletal muscle, liver and fat cells. The pancreas normally releases insulin after a meal to help transport glucose into the body's cells where the glucose is needed for energy production. Since cells must have glucose to survive, the body compensates by producing more insulin when a state of insulin resistance exists. This results in a high level of insulin in the blood (hyperinsulinemia) and high blood glucose (hyperglycemia) and consequent overstimulation of some tissues. Over time the relationship between glucose and insulin is not balanced and without treatment may lead to health complications. Hyperinsulinemia and insulin resistance affects levels of the body's lipids. Blood triglycerides and LDL (low-density lipoprotein, the "bad cholesterol") go up while HDL (high-density lipoprotein, the "good cholesterol") decreases. Changes in lipids can cause fatty plaque deposits to form in the vasculature and lead to cardiovascular disease and strokes.

Insulin resistance and metabolic syndrome are two terms often used interchangeably. Metabolic syndrome is essentially a subset of insulin resistance conditions, including obesity, alterations in lipid levels and abnormal glucose processing.

In one view, insulin resistance is not a disease per se or even a specific diagnosis but rather a set of pathological conditions that reflect this particular malfunction of the cells in the body. Insulin resistance is often associated with type II diabetes (T2D), obesity, stress, cardiovascular disease, hypertension, polycystic ovarian syndrome and nonalcoholic fatty liver disease. Most people with insulin resistance may not show any obvious symptoms for many years. If the body's insulin production fails to keep up with demand, then high blood sugar will occur. Once blood glucose reaches a high enough level, T2D is present. T2D is characterized by high blood sugar in the context of insulin resistance and insufficient insulin. The high glucose level can damage blood vessels in many organs, including the kidneys. Insulin resistance is a risk factor for developing T2D. It has also been postulated that there may be a link between insulin resistance and some types of cancer.

The cause and mechanism of insulin resistance are not fully understood. Genetic factors, lifestyle, and faulty signaling pathways have been implicated. There is not a single, or even a clearly defined set of genes responsible for the development of T2D. Insulin resistance can be viewed as an inflammatory disease with defective immune signaling. Many cytokines and chemokines are associated with this pathology. Examples include adiponectin, leptin, TNF alpha, interleukins IL-1 and IL-6, IL-3, IL 4-7, and the functions of the family of Toll-Like Receptors (TLR) such as TLR4, TLR7, and TLR9.

Various strategies are currently employed in the management of insulin resistance in T2D. Rates of T2D have increased markedly since 1960 in parallel with increasing obesity rates. Obesity is thought to be the primary cause of T2D in people who are genetically predisposed to the disease, except for people of East-Asian ancestry. In 2010, 285 million people were diagnosed with T2D compared to 30 million in 1985. T2D is typically a chronic disease associated with a 10 year shorter life expectancy. Long-term complications of high blood sugar include heart disease, ulcers of the skin, strokes, damaged eyesight, kidney failure, and poor blood flow in the limbs leading to amputations.

High blood sugar is only a symptom of T2D, not a cause. Modern therapies often target high glucose as the primary culprit of the disease. T2D is first managed by increasing physical exercise and dietary changes. If these measures do not sufficiently lower blood sugar, medications are employed. The most commonly used drug, insulin in various formulations, is used to lower blood glucose. Metformin, a biguanide drug, inhibits glucose production and release by the liver. By cutting off the glucose supply, metformin increases insulin sensitivity. Other therapies include insulin sensitizers, such as thiazolidinedione drugs Avandia and Actos, which lower blood glucose. They attach to the insulin receptors on cells in the body and cause the cells to become more responsive to insulin and remove more glucose from the blood. Insulin secretagogues increase insulin production and release by pancreas. The incretin-related drugs, glucagon-like peptide-1 (GLP-1) receptor agonists (GLP-1 RAs) and dipeptidyl peptidase-4 (DPP-4) inhibitors that disable degradation of GLP-1 also facilitate tissue uptake of glucose. Sodium-glucose co-transporter 2 (SGLT2) inhibitors increase glucose elimination in urine, and alpha-glucosidase inhibitors help limit degradation of glucose precursors in the gut.

Current treatments do not however reduce the incidence or effect cure. All present drugs have side effects that range from mild to life-threatening and these side effects frequently warrant FDA 'Black Box' warnings. One of the most common problems with T2D drugs is the induction of lactic acidosis (LA). LA occurs when too much lactic acid builds up in the body and can be fatal. Traditional therapies available to patients with type T2D after metformin failure, sulphonylureas and thiazolidinediones are often associated with weight gain, hypoglycemia or poor long-term efficacy.

No present T2D drugs address the progressive nature of disease and the underlying cause, insulin resistance. There is a need for agents with prolonged efficacy, disease modification, and improved safety.

SUMMARY

In some aspects, embodiments herein relate to methods of treating insulin resistance comprising administering to a subject a pharmaceutical composition comprising diethyl azelate.

In some aspects, embodiments herein relate to methods of treating insulin resistance comprises orally administering to a subject a pharmaceutical composition that includes diethyl azelate at a dosage range from about 0.1 mg/kg/day to about 10 mg/kg/day.

BRIEF DESCRIPTION OF DRAWINGS

Various embodiments of the present disclosure will be described herein below with reference to the figures wherein.

Figure 1:
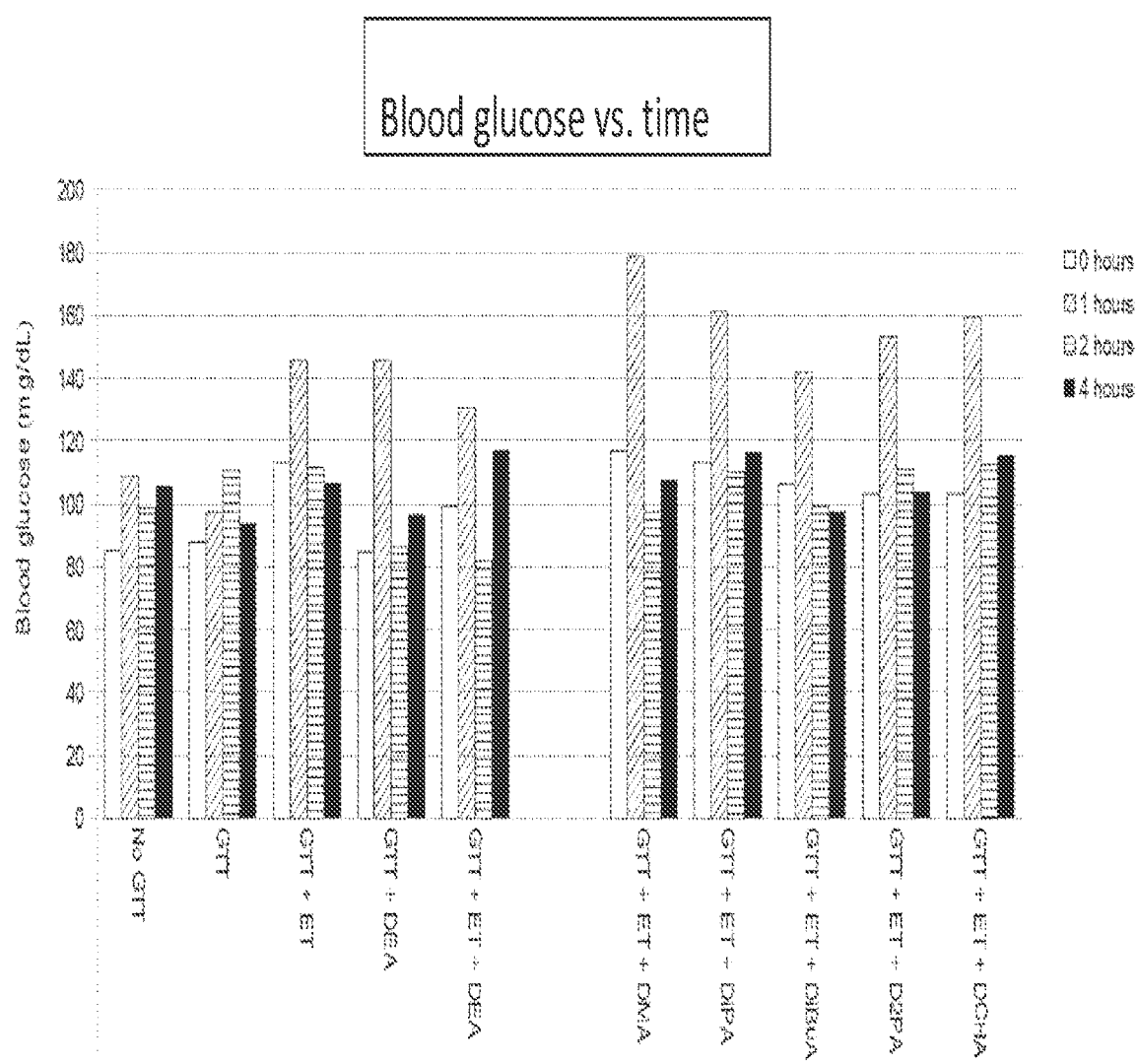
FIG. 1 shows a plot of aggregated data for the oral glucose test performed with various azelate esters against a series of control experiments.

Abbreviations: GTT; glucose tolerance test, ET; ethanol, DEA; diethyl azelate, OMA; dimethyl azelate, DiPA; di-isopropyl azelate, DiBuA; di-isobuty lazelate, D2PA; di-2-pentyl azelate; OCHA; dicyclohexyl azelate.

DETAILED DESCRIPTION

In embodiments, there are provided methods of treating insulin resistance comprising administering to a subject a pharmaceutical composition comprising diethyl azelate. In embodiments, the methods embrace treating diseases associated insulin resistance. In embodiments, the methods embrace treating insulin resistance in obesity and type 2 diabetes. In further embodiments, the methods embrace alleviating of insulin resistance in obesity and type 2 diabetes.

"Diabetes" refers to a group of metabolic diseases characterized by high blood sugar (glucose) levels which result from defects in insulin secretion or action, or both.

"Type 2 diabetes" or "T2D" refers to one of the two major types of diabetes, the type in which the beta cells of the pancreas produce insulin, at least in the early stages of the disease, but the body is unable to use it effectively because the cells of the body are resistant to the action of insulin. In later stages of the disease the beta cells may stop producing insulin. Type 2 diabetes is also known as insulin-resistant diabetes, non-insulin dependent diabetes and adult-onset diabetes.

"Pre-diabetes" refers to one or more early diabetes-related conditions including impaired glucose utilization, abnormal or impaired fasting glucose levels, impaired glucose tolerance, impaired insulin sensitivity and insulin resistance.

"Insulin resistant" refers to the condition when cells become resistant to the effects of insulin—a hormone that regulates the uptake of glucose into cells—or when the amount of insulin produced is insufficient to maintain a normal glucose level. Cells are diminished in the ability to respond to the action of insulin in promoting the transport of the sugar glucose from blood into muscles and other tissues (i.e. sensitivity to insulin decreases). Eventually, the pancreas produces far more insulin than normal and the cells continue to be resistant. As long as enough insulin is produced to overcome this resistance, blood glucose levels remain normal. Once the pancreas is no longer able to keep up, blood glucose starts to rise, resulting in diabetes. Insulin resistance ranges from normal (insulin sensitive) to insulin resistant (IR).

"Obesity" refers to a chronic condition defined by an excess amount body fat. The normal amount of body fat (expressed as percentage of body weight) is between 25-30% in women and 18-23% in men. Women with over 30% body fat and men with over 25% body fat are considered obese.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When numerical ranges of values are disclosed, such ranges are intended to include the numbers themselves and any sub-range between them. This range may be integral or continuous between and including the end values.

The term "combination therapy" means the administration of two or more therapeutic agents to treat a therapeutic condition or disorder described in the present disclosure. Such administration may encompass co-administration of these therapeutic agents in a substantially simultaneous manner, such as in a single dosage form having a fixed ratio of active ingredients or in multiple, separate dosage forms for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing the impact of, or eliminating the disease or disorder.

As used herein, reference to "treatment" of a subject is intended to include prophylaxis. The term "subject" means all mammals including humans. Examples of patients include humans, cows, dogs, cats, goats, sheep, pigs, and rabbits. In particular embodiments, the subject is a human.

As used herein, the term "comprising" is intended to mean that the compositions and methods include the recited elements, but not excluding others. The term "consisting essentially of," as applied to the compositions of the present embodiments, means the composition can contain additional elements as long as the additional elements do not materially alter the composition. The term "materially altered," as applied to a composition, refers to an increase or decrease in the therapeutic effectiveness of the composition as compared to the effectiveness of a composition consisting of the recited elements. In other words, "consisting essentially of" when used to define compositions, shall mean excluding other components of any essential significance to the composition. Thus, a composition consisting essentially of the components as defined herein would not exclude trace contaminants from the isolation and purification method and pharmaceutically acceptable carriers. "Consisting of" shall mean excluding more than trace elements of other ingredients and substantial method steps for administering the compositions of this invention. Embodiments defined by each of these transition terms are within the scope of this invention.

A "therapeutically effective" amount, as used herein, is an amount that is sufficient to provide some improvement or benefit to the subject. Alternatively stated, a "therapeutically effective" amount is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

Pharmaceutical Compositions And Treatments Thereof

While it may be possible for the compounds disclosed herein to be administered as the raw chemical, it is also possible to present them as a pharmaceutical composition. Accordingly, provided herein are pharmaceutical compositions which include one or more of certain compounds disclosed herein, in particular at least diethyl azelate, together with one or more pharmaceutically acceptable carriers thereof and optionally one or more other therapeutic ingredients. Diethyl azelate may be found in some common foods (Yu 2001; Plough, Zhangxia et al. 2002; Kim and Chung 2008; Fan, Fan et al. 2015) and is an approved flavoring additive at gram quantities, in the EU (AFC 2005).

In some embodiments, the pharmaceutical composition include diethyl azelate. In some embodiments, the pharmaceutical composition include diethyl azelate and a second active ingredient.

The second active ingredient may include one or more of a C 1-C4 alkyl ester azelate (different from diethyl azelate), a biguanide, a thiazolidinedione, a corticosteroid, insulin, a lipase inhibitor, a glucagon-like peptide-1 (GLP-1) agonists and/or mimetics, and combinations thereof. Examples of $C_1$-$C_4$ alkyl ester azelate include diethyl azelate (DMA) dimethyl azelate, (DiPA), di-isopropyl azelate (DiBuA), di-isobuty lazelate (D2PA), di-2-pentyl azelate (DCHA), dicyclohexyl azelate. $C_1$-$C_4$ alkyl ester azelate can be prepared from azelaic acid and the respective alcohols (e.g., methyl, ethyl, propyl, isobutyl, 1-, 2-, and 3-pentyl, and cyclohexyl) using the standard acid-catalyzed esterification. An aliphatic acid contains an alkyl group bound to the carboxyl group.

Other second active ingredients include, without limitation, alpha glucosidase inhibitors, dipeptidyl peptidase-4 (DPP-4) inhibitors, AKA incretin enhancers (including alogliptin, linagliptin, saxagliptin, sitagliptin, vildagliptin), sulfonylureas and related agents (including glibenclamide, gliclazide, glimepride, glipizide, tolbutamide and nateglinide, repaglinide), acarbose, sodium-glucose co-transporter 2 (SGL T2) inhibitors (e.g., canagliflozin, dapagliflozin, empagliflozin) and natural products such as nopal (prickly pear cactus), fenugreek, karela (bitter melon), gymnema, ginseng, tronadora, chromium, and alpha-lipoic acid, and hydroxycitric acid.

In some embodiments, the biguanide comprises metformin, buformin, phenformin, or combinations thereof.

Where compounds have been in disuse due to toxicity or other detrimental side effect, dosages may be substantially reduced compared to those that were originally approved.

In some embodiments, the thiazolidinedione includes pioglitazone, rosiglitazone, or combinations thereof.

In some embodiments, the corticosteroid includes prednisone.

In some embodiments, the insulin is formulated as a rapid-acting formulation, an intermediate-acting formulation, a long-acting formulation, or combinations thereof.

In some embodiments, the lipase inhibitor includes orlistat.

In some embodiments, the GLP-1 agonist includes exenatide, liraglutide, and combinations thereof. In some embodiments, the pharmaceutical composition consists essentially of diethyl azelate as active ingredient. In some embodiments, the pharmaceutical composition consists of diethyl azelate as active ingredient.

In some embodiments, the pharmaceutical composition is enterically coated. The pharmaceutical composition of the present embodiments can be configured for immediate release, extended release, sustained release, and controlled release of diethyl azelate. In some embodiments, the pharmaceutical composition is configured for extended release of diethyl azelate. In some embodiments, the pharmaceutical composition is configured for any combination of immediate release, extended release, sustained release, and controlled release of diethyl azelate. The various release profiles of the foregoing embodiments may be achieved via any conventional method known in the art. In some embodiments, the pharmaceutical composition is administered once daily. In some embodiments, the pharmaceutical composition is administered twice or thrice daily.

The carrier(s) are "acceptable" in the sense of being compatible with the other ingredients of the formulation and not deleterious to the subject. Proper formulation is dependent upon the route of administration chosen. Any of the well-known techniques, carriers, and excipients as understood in the art may be used e.g., those disclosed in Remington's Pharmaceutical Sciences. The pharmaceutical compositions disclosed herein may be manufactured in any manner known in the art, such as by means of conventional mixing, dissolving, granulating, dragee-making, levigating, emulsifying, encapsulating, entrapping or compression processes.

The pharmaceutical compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual, ocular, intranasal, and intraocular) administration although the most suitable route may depend upon for example the condition and disorder of the recipient. In particular embodiments, the pharmaceutical composition is suitable for oral administration. The pharmaceutical compositions may conveniently be presented in unit dosage forms and may be prepared by any of the methods well known in the art of pharmacy. Typically, these methods include the step of mixing diethyl azelate, and optionally any co-administered active ingredient disclosed herein, with the carrier which constitutes one or more accessory ingredients. In general, the pharmaceutical compositions are prepared by uniformly and intimately mixing the active ingredients with liquid carriers or finely divided solid carriers or both and then, as necessary, shaping the product into the desired composition.

Pharmaceutical compositions of diethyl azelate, an any optional secondary active ingredient, suitable for oral administration may be presented as discrete units such as capsules, cachets or tablets each containing a predetermined amount of the active ingredient(s); as a powder or granules; as a solution or a suspension in an aqueous liquid or a non-aqueous liquid; or as an oil-in-water liquid emulsion or a water-in-oil liquid emulsion. The active ingredient(s) may also be presented as a bolus, electuary or paste. For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein.

All pharmaceutical compositions for oral administration may be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Examples of fillers or diluents for use in oral pharmaceutical formulations such as capsules and tablets include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such in the case of the filler PROSOLV® (available from JRS Pharma). PROSOLV® is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. PROSOLV® comes in different grades based on particle size, and is a white or almost white, fine or granular powder, practically insoluble in water, acetone, ethanol, toluene and dilute acids and in a 50 g/L solution of sodium hydroxide.

Examples of disintegrants for use in pharmaceutical compositions such as capsules and tablets include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxypropyl cellulose, starch, pregelatinized starch, and sodium alginate.

Additionally, glidants and lubricants may be used in oral pharmaceutical compositions to ensure an even blend of excipients upon mixing. Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate. Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Examples of tablet binders include, without limitation, acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

Methods of Treatment

It has been discovered that azelate esters have beneficial effect on abnormal cellular communications. Diethyl azelate (DEA), in particular, is postulated to reversibly modulate immune function and protect against harmful effects of various chemicals and biological pathogens and are non-toxic to mammalian cells. This is significant because insulin resistance is postulated herein to be the result of malfunctioning of the immune system. Thus, embodiments herein provide methods of treating insulin resistance and/or diseases, conditions, or disorders associated with insulin resistance in subjects by administration of diethyl azelate alone, or optionally in conjunction with other therapies employed in this area known in the art. When used in combination with known therapies, the dosage of these otherwise toxic secondary active ingredients may be significantly reduced.

Reversal of insulin resistance in obese rodents was demonstrated using salicylates and was attributed to increasing insulin sensitivity. It is postulated herein that azelate esters may behave in a manner similar to salicylates, including diethyl azelate (DEA) in particular.

Without being bound by theory, it is postulated that diethyl azelate is particularly suited as a drug for insulin resistance/T2D because it modulates signaling pathways relevant to the disease, can be easily formulated for oral use and has an excellent safety profile. As disclosed herein and without being bound by theory, it is postulated that azelate esters, in general, exert activity in vitro and in vivo by modulating cytokine/chemokine signaling and host immune responses.

In some embodiments, the methods herein take advantage of the above connection between immune pathway modulation and T2D, thus providing methods that comprise an administering step performed enterically. In some such embodiments, the enteric administration is oral. Oral administration may be accomplished via tablet, elixir, or the like, as described herein above. In some embodiments, the administering step is performed parenterally. In some embodiments, the parenteral administration is performed intramuscularly or subcutaneously. In some embodiments, combinations of enteric and parenteral administration may be employed.

A suitable or effective single dose size is a dose that is capable of causing a measurable change in insulin resistance/sensitivity (e.g., a decrease in insulin sensitivity) of a subject when administered one or more times over a suitable time period. A suitable or effective single dose size can also be a dose that is capable of causing a measurable change in insulin resistance in a subject as compared to the measure of insulin resistance established prior to initiation of the treatment, when administered one or more times over a suitable time period. Doses can vary depending upon the condition of the subject being treated, including the severity of the insulin resistance, whether the subject suffers from overt diabetes or not, and/or any other related or non-related health factors experienced by a particular patient.

Typically, the method of the present invention comprises administering a pharmaceutical composition including diethyl azelate in a dose from about 0.1 mg/kg/day to about 10 mg/kg/day. In some embodiments, the dosage of diethyl azelate is in a range from about 0.5 mg/kg/day to about 5 mg/kg/day, from about 0.5 mg/kg/day to about 2.5 mg/kg/day, from about 0.5 mg/kg/day to about 1.5 mg/kg/day, or from about 0.8 mg/kg/day to about 1.2 mg/kg/day. In some embodiments, the diethyl azelate in the pharmaceutical composition is about 1 mg/kg/day. The dose range for an adult human is generally from 3 mg to 2 g per day. The dosage may be calculated based on the body mass of the subject. For example, based on an average body mass of from about 120 to about 180 kg, the dose range for an adult human may be from 50 mg to 0.5 g per day; based on an average body mass of from about 80 to about 120 kg, the dose range for an adult human may be from 10 mg to 1 g per day, or from 5 mg to 0.15 g per day; based on an average body mass of from about 60 to about 80 kg, the dose range for an adult human may be from 25 mg to 0.3 g per day. The pharmaceutical compositions may contain, for example, from about 0.1% to about 99% by weight, of diethyl azelate, depending on the method of administration. Where the pharmaceutical compositions comprise dosage units, each unit may contain, for example, from about 10 to 2000 mg, or from about 10 to 1000 mg of the active ingredient, more typically from 5 mg to 150 mg, in single or divided doses. Those skilled in the art may recognize the flexibility in dosing based on individual patient needs and dosages may be outside these ranges based on responses observed in tests such as the glucose tolerance test. Thus, these ranges should be understood to be merely exemplary. In some embodiments, a dosage is selected based on diagnostic screens as part of an ongoing treatment regimen, thus allowing for adjustment of the dosage as needed for each individual subject.

The methods may further include administering a second active ingredient. In some embodiments, administering the second active ingredient is separate from administering the pharmaceutical composition including diethyl azelate. In some embodiments, the second active ingredient is co-administered with the pharmaceutical composition including diethyl azelate. In some embodiments, the second active ingredient is present in the pharmaceutical composition including diethyl azelate.

In some such embodiments, the subject is fasting prior to the administering step. In other embodiments, the subject is not fasting prior to the administering step.

In some embodiments, there are provided uses of diethyl azelate in the manufacture of a medicament for the treatment of insulin resistance. In further embodiments, the medicament is prepared to be administered in a dosage range from about 0.5 mg/kg/day to about 5 mg/kg/day.

Testing for Type 2 diabetes typically involves drawing blood samples and measuring the glucose (sugar) levels within the blood. During a random glucose test, a sample of blood can be obtained and tested at any time. Normal random glucose levels are 70-110 mg/dl. According to the American Diabetes Association (ADA), a random glucose level of greater than 200 mg/dl is indicative of diabetes. During a fasting glucose test, a sample of blood is obtained following a period of not eating or drinking (except water) for at least 8 hours. It is usually drawn early in the morning, before breakfast. According to the American Diabetes Association, a fasting blood glucose level of greater than 125 mg/dl on two occasions is indicative of diabetes. The fasting blood glucose test is the most common test in use for diagnosing diabetes. During an oral glucose tolerance test, a fasting blood sugar is obtained initially. The subject is then asked to drink a sweet sugary beverage, e.g., Glucola (containing 50% dextrose 175 g dextrose in 150 ml solution). Blood glucose levels are then obtained every 30 minutes for the next 2 hours. A blood glucose level below 140 mg/dl at 2 hours is considered normal. A blood glucose level of greater than 200 mg/dl at 2 hours is indicative of diabetes. A blood glucose level of 140-200 mg/dl at 2 hours indicates some impairment abnormality in glucose tolerance.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1

This example describes the preparation and characterization of azaleic acid esters.

Azelaic acid esters were synthesized from azelaic acid and respective alcohols (methyl, ethyl, propyl, isobutyl, 1-, 2-, and 3-pentyl, and cyclohexyl) using the standard acid-catalyzed esterification followed by fractional distillation to produce; dimethyl azelate (DMA), diethyl azelate (DEA), di-diisopropyl azelate DIPA, di-diisobutyl azelate (DiBU), di-(1-pentyl) azelate (D1 PA), di-(2-pentyl) azelate (D2PA), di-(3-pentyl) azelate (D3PA), and dicyclohexyl azelate (DCHA). These compounds may be further referred to together as "the azelates."

In Silico Toxicity: Derek™ for Windows_11.0.0 (Lhasa Ltd, UK) was used to perform predictive toxicity of the azelates for bacterium and mammal species. No toxicity was predicted for any of the azelates.

Genotoxicity Ames test: Potential toxicity of the azelates was examined using ChromoTest S9 activation enzymes (EBPI, Canada). The azelates were tested at 0.0006%-10% corresponding to potential clinical dose ranges. The azelates showed no trace of genotoxicity.

Azelate esters broadly downregulate signaling: This experiment using panels of 47 biomarkers demonstrated that contrary to classical pharmacology, individual azelates exert unique and different biochemical effects that are also different from the parent compound, azelaic acid, and thus cannot be viewed as simple pro-drugs.

EpiDerm 3-D human skin tissue (MatTek) was exposed to an irritant, croton oil+the azelates for 24 hours. Levels of 47 cytokines and other signaling molecules were measured in cultured media and tissue lysates using multiplex immunoassays. Relative % differences in levels of select markers in medium and tissues after treatment with croton oil plus azelates versus croton oil alone were graphed as heat maps displaying statistically significant/nearly significant differences and distinct patterns of marker modulation. The azelates also exerted chemoprotective activity against croton oil damage on microscopic examination. Diethyl azelate activity, in particular, was found to be relevant to T2D therapy because it downregulated multiple cytokines relevant to T2D including IL-1 a, IL-6, IL-8, and TNF-a.

The azelates modulated broad-range signaling of pathogen-associated molecular patterns (PAMP) receptors: Toll-Like Receptors (TLRs) are a class of PAMP receptors. Various PAMP receptor agonists (ligands); nineteen discrete entities, were added to dendritic cells along with 0.5% diethyl azelate (DEA) and measured levels of 34 signaling molecules (ATP, cytokines, chemokines) produced by the cells after 24 hours. To assess if DEA affected PAMP receptor signaling, the ratios of the levels of these molecules were calculated in treated and untreated cells. If DEA had no effect, these ratios would be equal to 1. Using ATP as an example, it was clear that DEA decreased signaling induced by most TLR agonists. A similar effect of DEA was observed on the ratios of other signaling molecules. DEA affected signaling of all PAMP receptors but the effect was greater for the receptors localized on the cell surface than for these inside the cell. These results support the idea that DEA exerts non-specific effects on signaling of diverse PAMP receptors, in particular the TLRs implicated in pathology of T2D.

Figure 2:
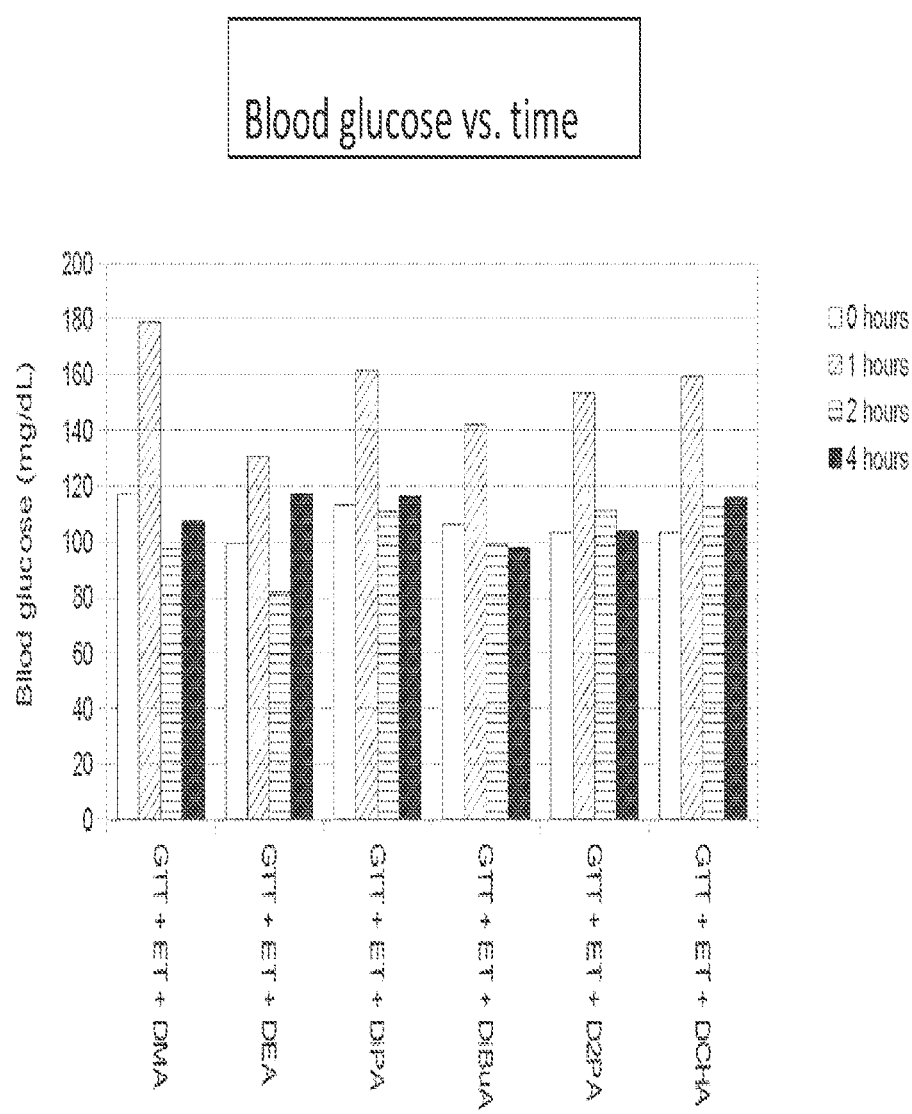
FIG. 2 shows a plot of aggregated data for the oral glucose test performed with various azelaic acid esters as in FIG. 1, but without the controls for ease of comparing the impact of the different azelates.
Figure 3:
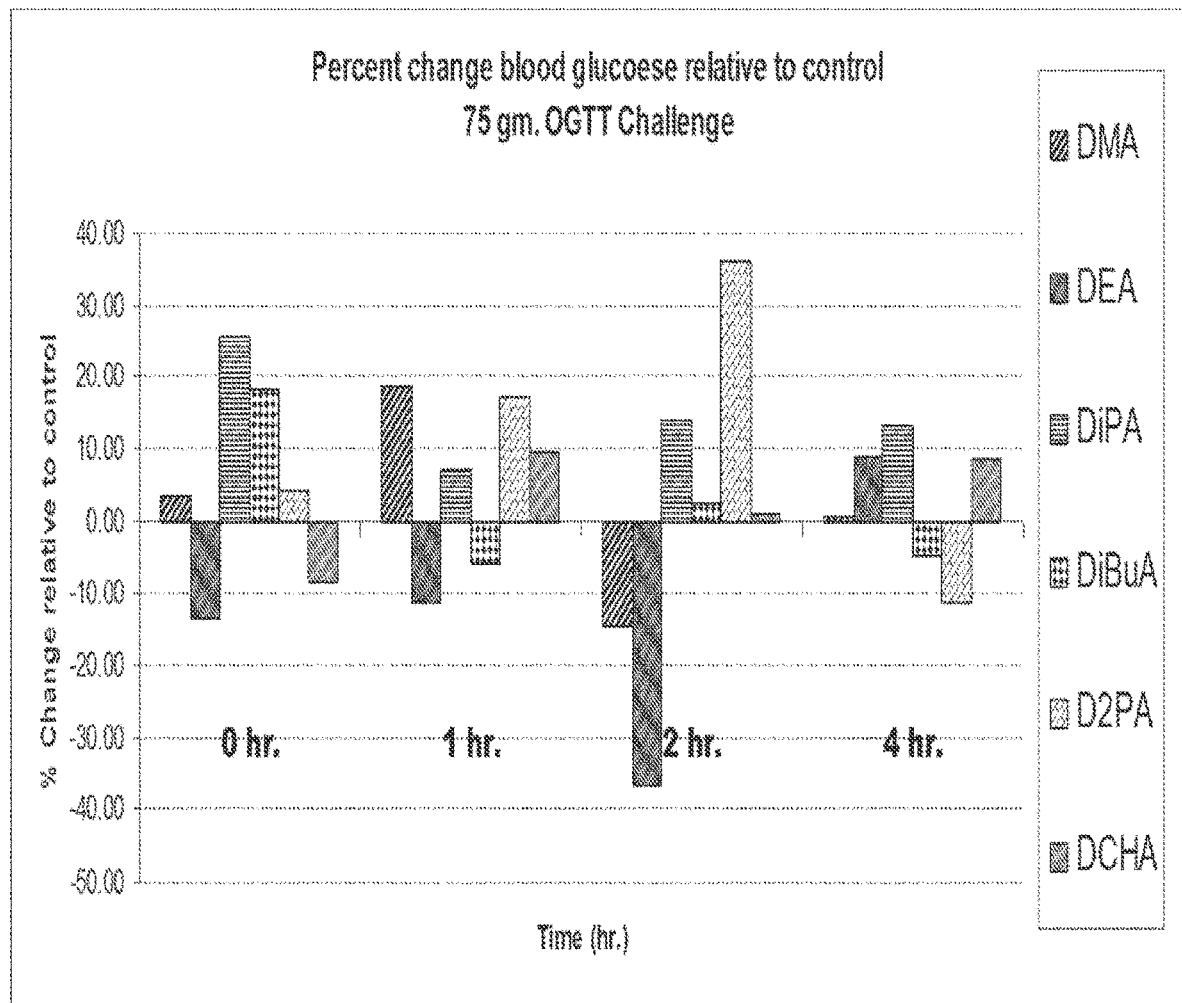
FIG. 3 shows a plot of aggregated data comparing the percent change in blood glucose relative to untreated control state (ethanol-induced insulin resistance) for the oral glucose test performed with various azelaic acid esters.

The azelates significantly reduced blood glucose in an induced insulin resistance state in a human self-study. An insulin resistance state was induced by consumption of 50 ml ethanol plus diethyl azelate at 1 mg/kg administered orally 8 hours prior to a standard oral glucose tolerance test (OGTT). OGTT was performed with a dose of 75 g glucose in an aqueous solution. Blood glucose was measured at 0, 1, 2 and 4 hours. Average results of 10 separate experiments expressed as percentage changes in blood glucose due to diethyl azelate treatment indicated significant decrease of glucose at the baseline (fasting) and highly significant ($p<0.0001$) at the peak postprandial time point at 2 hours. FIGS. 1-3 summarize the data from these tests. Comparing this data with clinical data available on metformin indicated a clinical advantage of diethyl azelate over metformin.

FIG. 1 shows the results of blood glucose measurements over time (fasting; t=0 and at t=1, 2, and 4 hours) in examined treatment regimens: no GTT, GTT, GTT after ethanol-induced insulin resistance (GTT+ET), diethyll azelate effect without ethanol-induced insulin resistance (GTT+DEA), and diethyl azelate effect with ethanol-induced insulin resistance (GTT+ET+DEA). The hyperglycemic effect of ethanol and the hypoglycemic effect of diethyl azelate can be readily observed.

FIG. 2 highlights the differences between six different azelates on blood glucose over time. Notably, the time-dependent effects of the six azelates showed distinct and unique patterns at each time point (0, 1, 2, and 4 hours). Such differences were unexpected and there was no observed activity trend based on chemical structure similarities in the series of azelates screened. Thus, the conventional notion that simple homologues should display similar activity does not hold. Without being bound by theory, it is postulated that different azelate esters may have a differential impact on cell membrane plasticity resulting in very different downstream effects in modulating cell signaling pathways. Thus, the effectiveness of modulating any particular pathway in connection with favorable treatment of insulin resistance could not have been predicted based on chemical structure via traditional structure-activity relationships (SARs).

FIG. 3 shows the percent change in blood glucoses relative to untreated control state (ethanol-induced insulin resistance) at each time point (0, 1, 2, and 4 hours).

Figure 4:
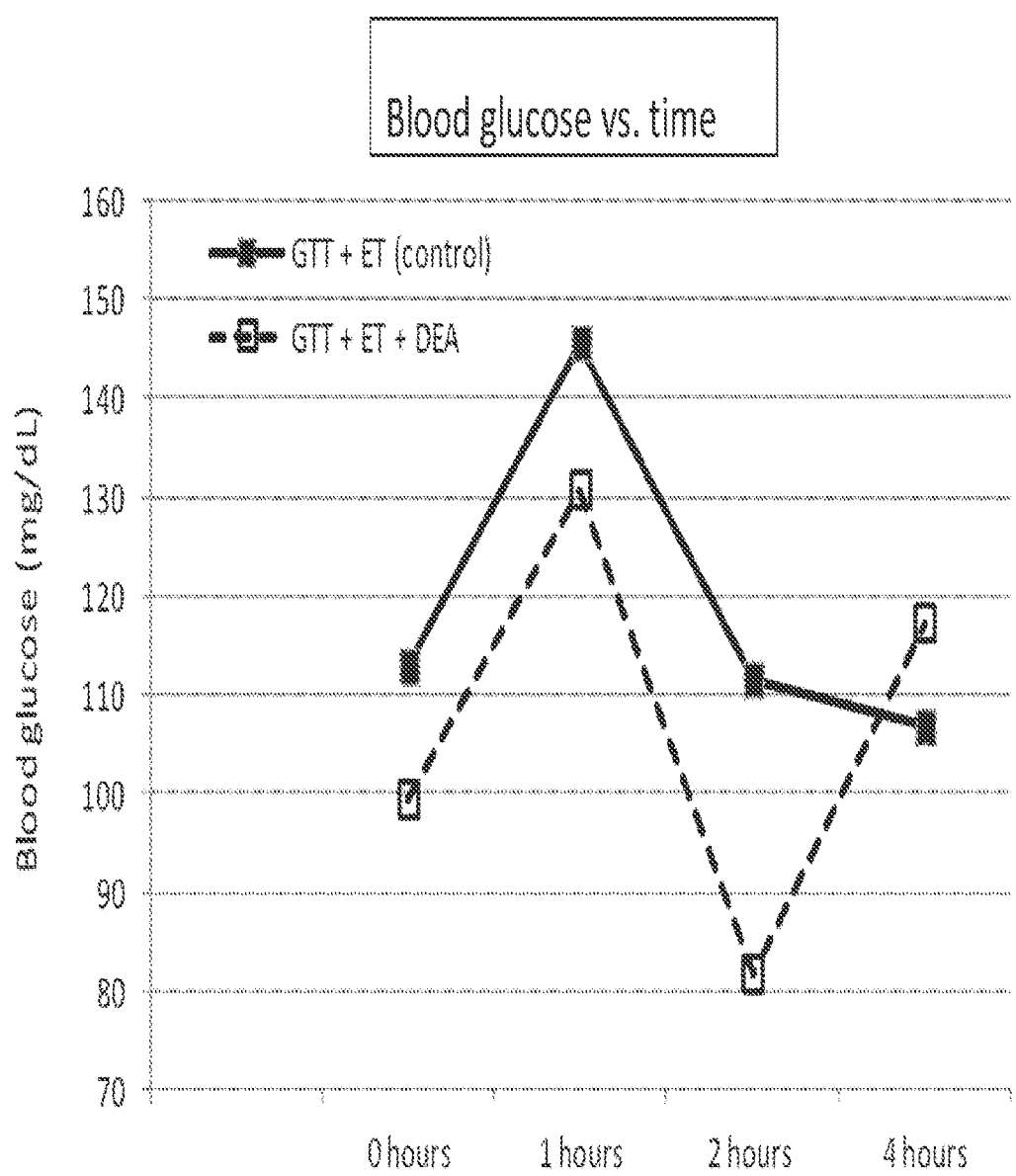
FIG. 4 shows a plot of aggregated data or the oral glucose test performed with diethyl azelate against a control.

FIG. 4 illustrates the effect of diethyl azelate in ethanol-induced hyperglycemia on blood glucose levels compared to the untreated control state (ethanol-induced insulin resistance). The percentage decrease of glucose levels due to diethyl azelate treatment at fasting (t=0) was 13.6% (p=0.02; statistically significant), at t=1 hour was 11.4% (statistically not significant), and at t=2 hours was 36.7% ($p=6\times10-6$, statistically highly significant). A small (8.8%) increase in glucose level at t=4 hours was not statistically significant.

Example 2

Human Clinical Trial of the Safety and Tolerability of Diethyl Azelate

Objective

To evaluate the safety and tolerability of diethyl azelate (immediate release form) when administered orally to insulin resistant adult male volunteers, and to evaluate the change from baseline of selected biomarkers and computational indices of dysmetabolism when diethyl azelate is administered orally to insulin resistant adult male volunteers.

Subjects

A total of eight subjects were screened, out of which four subjects satisfied all the eligibility criteria. Three healthy male volunteers ranging between 18-50 years of age weighing between 80-120 kg were enrolled in the study. At screening, subjects were non-diabetic insulin resistant (NDIR) having a fasting plasma glucose of greater than 75 mg/dL and less than 126 mg/dL and have a compensatory hyperinsulinemia having a mean of two consecutive fasting insulin samples collected between 10 to 30 minutes apart of great than 12 µIU/mL. Subjects had no clinically significant illness that may affect glucose metabolism, insulin sensitivity or makes them otherwise unsuitable for inclusion in the study. Subjects had no history or ongoing significant abnormalities or diseases, in the areas, such as, endocrine, gastrointestinal, cardiovascular, hematological, renal, upper or lower respiratory, neoplasia. Subjects had no uncontrolled blood pressure of greater than 160/95 mmHg at screening. Subjects had a HbA1c level or less than 6.4%. Subjects had not used antidiabetic or antihyperglycemic medications in the last 6 months. Subjects had not used tobacco or nicotine containing products in the last 3 months. Subjects were not mentally or legally incapacitated. Subjects had no history of significant psychiatric disorder (within the last 10 years) and had no significant emotional problems at the time of the study. All subjects were evaluable for safety and all blood collections for pharmacokinetic analysis were collected as scheduled. All studies were performed with institutional review board approval and patient consent. The Board was constituted and operated in accordance with the principles and requirements described in the US Code of Federal Regulations (21 CFR Part 56). The board was ICH compliant.

Study Design

This study was an open label test/retest study measuring the change from baseline of selected biomarkers and computational indices of insulin sensitivity of the adult male volunteers in response to multiple doses of diethyl azelate. The study population was restricted to male participants in order to control for the variability associated with the menstrual cycle on the metabolic parameters of interest (Sheu, Chen et al. 2003). Baseline parameters were assessed followed by retest assessments at three weeks (21-days) post-dose.

Diethyl azelate (density of 0.973 g/mL at 25° C. or 973 mg/mL) was administered orally by needless syringes once a day at 1 mg/kg to each subject for 21 days starting at Day 1. The dose was calculated as described below, with standard rounding conventions applied to the nearest 0.01 mL:

1 mg/kg×Participant Weight (kg)×(1 mL/973 mg)=$X$ mL to Dose

Additional marketed pharmaceutical products were administered as part of the study procedures or as challenge agents associated with the Oral Glucose Tolerance (OGTT). These include 75 g CHO (carbohydrate) Glucola and small volumes of 0.9% Normal Saline administered intravenously secondary to blood collection. Subjects were evaluated with a baseline OGTT on Day 1 and a final OGTT on Day 21. Safety assessments were performed on each subject during the course of the study including clinical examination, vital signs recording, ECG recording, adverse event (AE) monitoring, and concomitant medication assessment.

Oral Glucose Tolerance Test (OGTT)

An Oral Glucose Tolerance Test (OGTT) was performed at baseline on Day 1 and Day 21. The OGTT was performed after a fast greater than eight hours and consisted of eight blood collections. Subjects were administrated a bottle of Glucola drink (containing 50% dextrose I 75 g dextrose in 150 mL solution; available as GlucoCrush™) over a course of five minutes, starting at T=0 (first sip of the Glucola). Two blood-draws occurred ~30 minutes and just prior (~0 minute) to administration of the Glucola. Post-meal blood collection occurred at 30, 60, 90, 120, and 180 minutes. Samples for glucose and exploratory PK and biomarker samples were collected at all timepoints associated with the OGTT. A detailed schedule of OGTT procedure assessments was shown in Table 1 below.

TABLE 1

| Timepoint | Blood Glucose (0.5 mL YSI) | Exploratory PK and Biomarker Samples |
| --- | --- | --- |
| −30 minute | X | X |
| −5 minute | X | X |
| 0 minute | X | X |
| 0 minute | Begin Consuming 75 g CHO Glucola | |
| 5 minute | Finish Consuming 75 g CHO Glucola | |
| 30 minute | X | X |
| 60 minute | X | X |
| 90 minute | X | X |
| 120 minute | X | X |
| 180 minute | X | X |

Results

Figure 5:
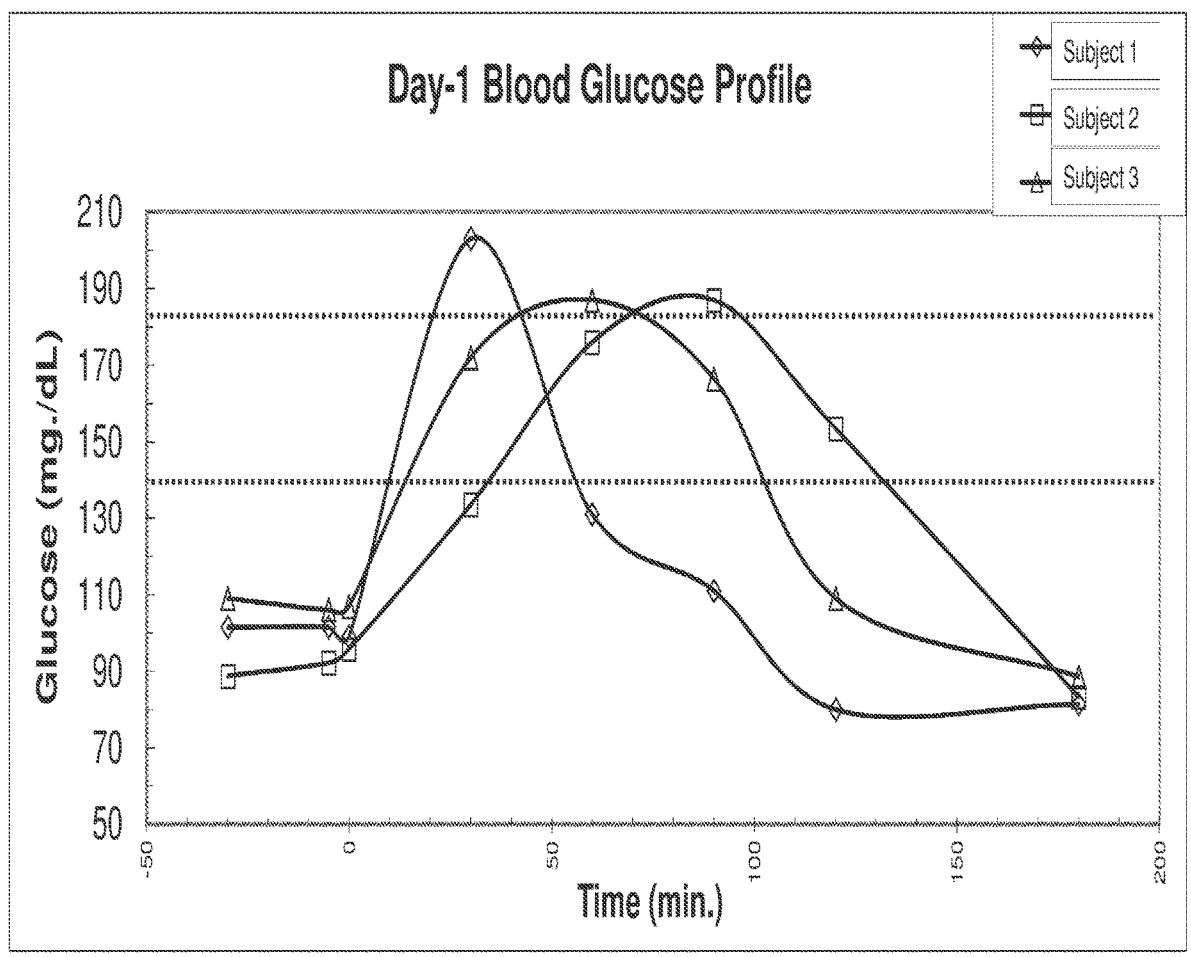
FIG. 5 shows profiles of blood glucose excursions obtained from three human subjects on Day 1 (prior to administration of diethyl azelate).
Figure 6:
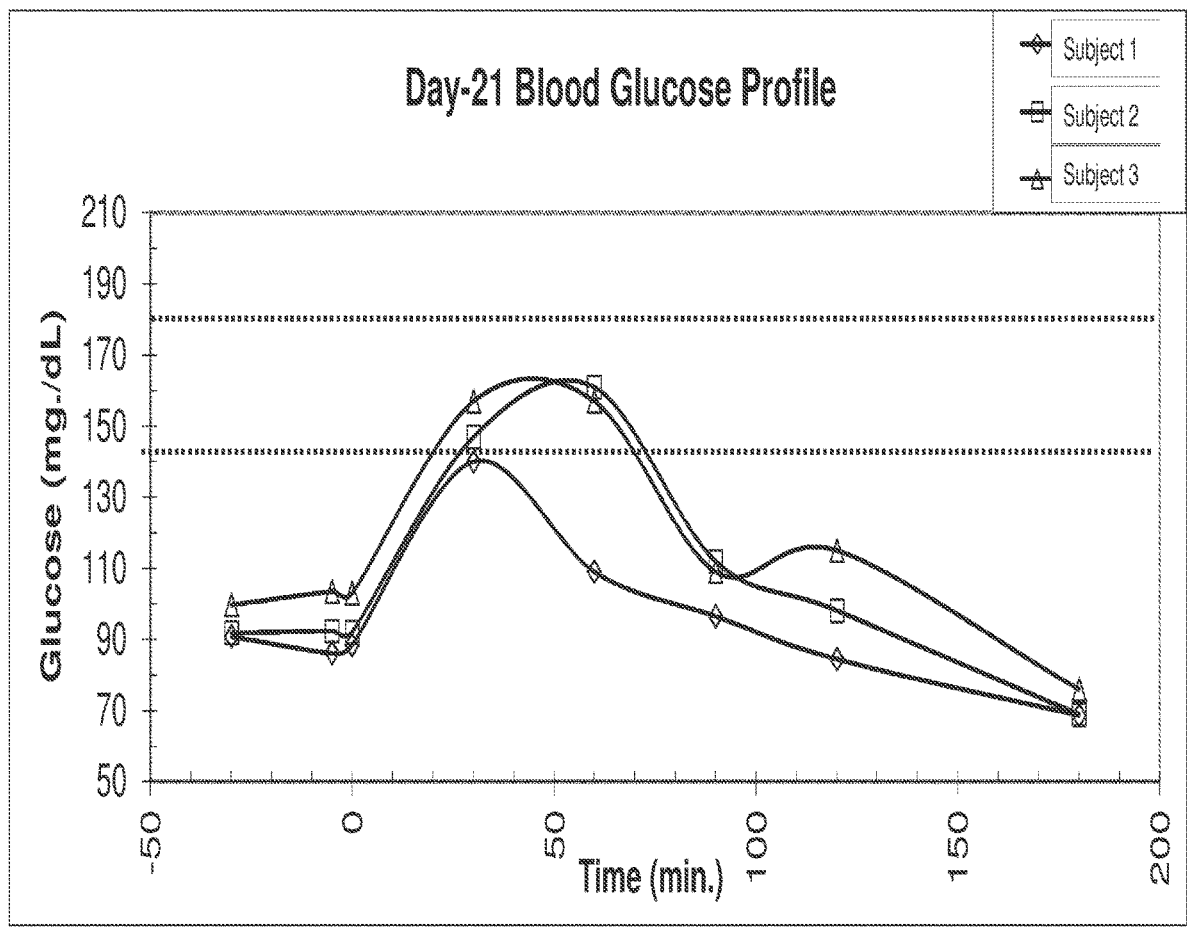
FIG. 6 shows profiles of blood glucose excursions obtained from three human subjects on Day 21 (after administration of last dose of diethyl azelate).
Figure 7:
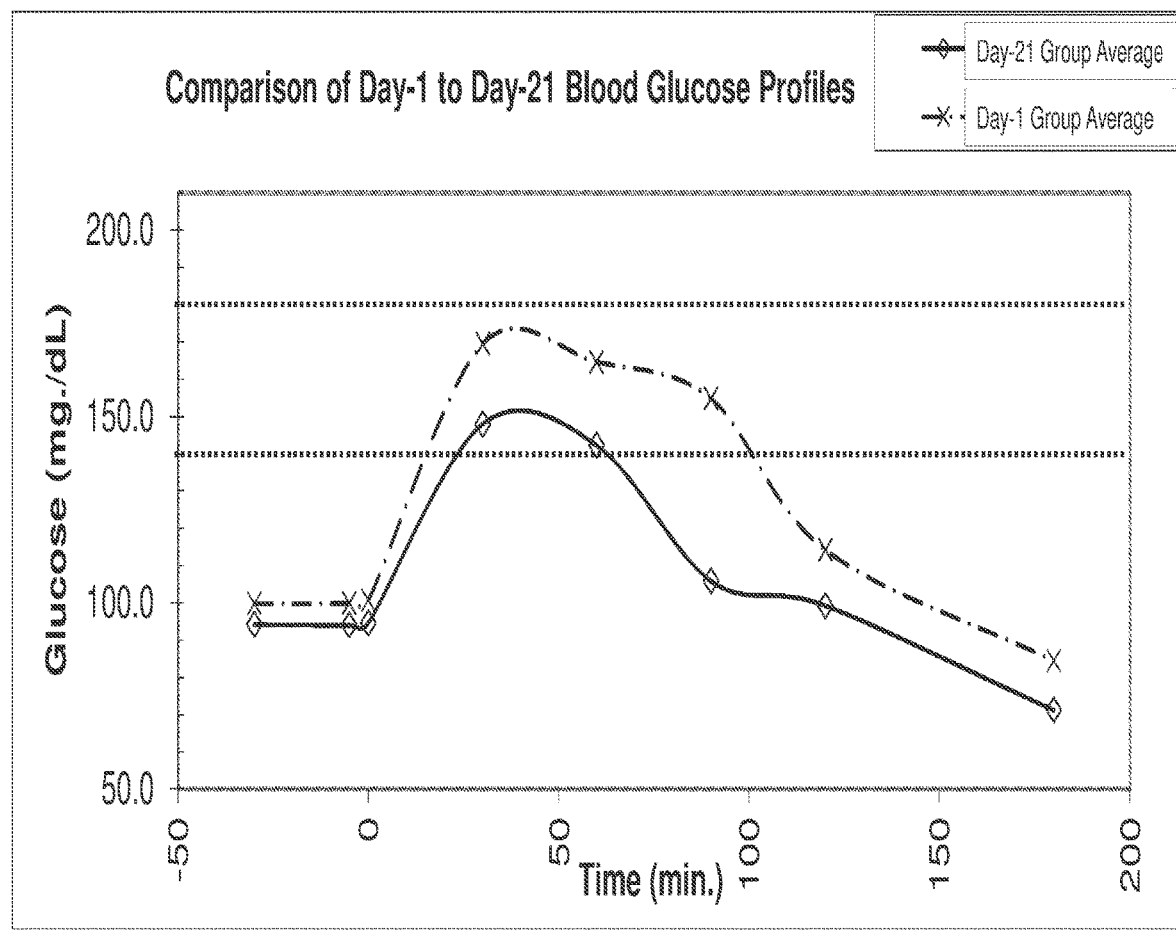
FIG. 7 compares the average blood glucose profiles obtained on Day-1 and Day-21.

The subjects were administered a dose of diethyl azelate (dose amount dependent of body weight) once a day for 21 days starting on Day-1. On Day-1, the OGTT was performed and completed on each subjects prior to first dosing yes. FIG. 5 displays the blood glucose profiles (fasting blood glucose levels) for the three single subjects on Day-1 obtained according to the schedule of OGTT procedure assessments, During the 3-week's treatment course, each subject took a total of 21 doses of diethyl azelate. FIG. 6 displays the blood glucose profiles (fasting blood glucose levels) for the three single subjects on Day-21 obtained according to the schedule of OGTT procedure assessments. The OGTT was performed within 10 minutes after the administration of the last dose of diethyl azelate. Table 2 summarizes the blood glucose levels of the group average of the Day-1 and Day-21, i.e., sum of blood glucose levels of three subjects/number of subjects (3), and the percent changes in the average blood glucose levels of these two groups, i.e., (difference between blood glucose level of Day-1 group average and Day-21 group average/blood glucose level of Day-21 group average)×100%. FIG. 7 displays the blood glucose profiles of the group average of Day-1 and Day-21. The data shows that the average blood glucose levels of the Day-1 group average (post-treatment) was significantly lower than that of the Day-21 group average (pre-treatment). For example, after the 3-weeks treatment course. The subject's average blood glucose levels had dropped to below 150 mg/dl (at T=30 mins, and 60 mins) as compared to the pre-treatment average blood glucose levels at ranges between 164 to 170 mg/dl.

All three subjects who had, prior to treatment, exhibited signs of insulin resistance and or T2D exhibited normal healthy insulin metabolism profiles after 21 days of DEA treatment. The dotted lines represent the 1 hour (180 mg/dl) and 2 hour (140 mg/dl) OGTT thresholds.

TABLE 2

OGTT Blood Glucose Levels mg/dL

| | Time (min.) | | | | | | | |
| --- | --- | --- | --- | --- | --- | --- | --- | --- |
| | −30 | −5 | 0 | 30 | 60 | 90 | 120 | 180 |
| Day-1 Group Average | 99.8 | 99.9 | 100.6 | 169.5 | 164.7 | 154.8 | 114.2 | 84.5 |
| Day-21 Group Average | 94.1 | 94.0 | 94.5 | 148.0 | 142.3 | 105.8 | 99.2 | 71.2 |
| Percent change: Day-1 vs. Day-21 | 6.0 | 6.2 | 6.5 | 14.5 | 15.7 | 46.3 | 15.1 | 18.6 |

Orally administered single doses of diethyl azelate was well tolerated by the three healthy male subjects. One subject (i.e., the fourth eligible subject) was discontinued from the study because of unrelated family health issues. The only observed adverse event observed was loose stools in one subject. No other subjects exhibited any adverse event. There were no clinically meaningful drug-related changes in physical examinations, vital signs, or electrocardiograms (ECGs).

What is claimed is:

1. An orally administrable pharmaceutical formulation comprising an amount effective to treat insulin resistance of from about 5 mg to 150 mg diethyl azelate as an active ingredient, and a pharmaceutically and orally acceptable carrier, excipient, or mixtures thereof, wherein the composition provides a superior reduction in blood glucose levels in insulin resistant subjects, when compared to the blood glucose levels of insulin resistant subjects administered formulations comprising other dialkyl azelates.

2. The pharmaceutical formulation of claim 1, wherein the pharmaceutical composition further comprises a second active ingredient.

3. The pharmaceutical formulation of claim 2, wherein the second active ingredient comprises one or more of the followings: a biguanide, a thiazolidinedione, a corticosteroid, insulin, a lipase inhibitor, a glucagon like peptide-1 (GLP-1) agonist, and a $C_1$-$C_4$ alkyl ester azelate different from diethyl azelate.

4. The pharmaceutical formulation of claim 3, wherein the biguanide comprises metformin, buformin, phenformin, or combinations thereof.

5. The pharmaceutical formulation of claim 3, wherein the thiazolidinedione comprises pioglitazone, rosiglitazone, or combinations thereof.

6. The pharmaceutical formulation of claim 3, wherein the corticosteroid comprises prednisone.

7. The pharmaceutical formulation of claim 3, wherein the insulin is formulated as a rapid-acting formulation, an intermediate-acting formulation, a long-acting formulation, or combinations thereof.

8. The pharmaceutical formulation of claim 3, wherein the lipase inhibitor comprises orlistat.

9. The pharmaceutical formulation of claim 3, wherein the GLP-1 agonist comprises exenatide, liraglutide, and combinations thereof.

10. The pharmaceutical formulation of claim 1 configured for immediate release, extended release, sustained release, or controlled release of diethyl azelate.

11. The pharmaceutical formulation of claim 1, wherein the pharmaceutical composition is enterically coated.

12. A pharmaceutical formulation for use in the treatment of insulin resistance comprising an amount effective to treat insulin resistance of from about 10 mg to 1,000 mg diethyl azelate as an active ingredient, and a pharmaceutically acceptable carrier, excipient, or mixtures thereof, wherein the composition provides a superior reduction in blood glucose levels in insulin resistant subjects, when compared to the blood glucose levels of insulin resistant subjects administered formulations comprising other dialkyl azelates.

13. The pharmaceutical formulation of claim 12, wherein the diethyl azelate is present in an amount of from about 10 mg to 150 mg.

14. The pharmaceutical formulation of claim 12, wherein the pharmaceutical composition further comprises a second active ingredient.

15. The pharmaceutical formulation of claim 14, wherein the second active ingredient comprises one or more of the followings: a biguanide, a thiazolidinedione, a corticosteroid, insulin, a lipase inhibitor, a glucagon like peptide-1 (GLP-1) agonist, and a $C_1$-$C_4$ alkyl ester azelate different from diethyl azelate.

16. The pharmaceutical formulation of claim 12, wherein the pharmaceutical composition is suitable for oral administration.

17. The pharmaceutical formulation of claim 16, wherein the pharmaceutical composition is enterically coated.

* * * * *